United States Patent [19]

Woog et al.

[11] 4,159,715

[45] Jul. 3, 1979

[54] LIQUID TREATMENT APPARATUS FOR BODY CARE

[75] Inventors: Philippe G. E. Woog, Vesenaz; Michel A. Moret, Chene Bourg; Pierre-Jean Jousson, Geneva; Jean-Pierre Musy, Puplinge, all of Switzerland

[73] Assignee: Les Produits Associes LPA S.A., Switzerland

[21] Appl. No.: 861,708

[22] Filed: Dec. 19, 1977

Related U.S. Application Data

[63] Continuation-in-part of Ser. No. 704,330, Jul. 12, 1976, Pat. No. 4,078,558.

[30] Foreign Application Priority Data

Dec. 28, 1976 [CH] Switzerland ................ 16365/76
Dec. 28, 1976 [CH] Switzerland ................ 16366/76
May 26, 1977 [CH] Switzerland ................ 6484/77
Nov. 28, 1977 [CH] Switzerland ................ 14517/77

[51] Int. Cl.$^2$ ............................................. A61H 9/00
[52] U.S. Cl. ................................. 128/66; 128/62 A
[58] Field of Search .............. 128/65, 66, 62 A, 230; 259/18, DIG. 44; 134/93, 100, 184

[56] References Cited

U.S. PATENT DOCUMENTS

| | | | |
|---|---|---|---|
| 2,849,159 | 8/1958 | Kaufmann | 128/230 |
| 3,044,465 | 7/1962 | Anderson et al. | 128/230 |
| 3,495,587 | 2/1970 | Freedman | 128/66 |
| 3,669,101 | 6/1972 | Kleiner | 128/66 |
| 3,820,532 | 6/1974 | Eberhardt et al. | 128/66 |

Primary Examiner—Lawrence W. Trapp
Attorney, Agent, or Firm—Kane, Dalsimer, Kane, Sullivan and Kurucz

[57] ABSTRACT

An apparatus for personal hygiene which includes a reservoir for containing liquid to be applied to selected parts of the body is provided with a dispenser containing a dentifrice to be dispensed therefrom upon demand. The dispenser is adapted to be housed in the bottom part of the casing of the apparatus. The dispenser is provided with a dentifrice container closed at the bottom by a flexible membrane and with an intermediate wall located above this membrane defining upper and lower container compartments. The intermediate wall includes an opening which permits communication between the two compartments. A closure finger attached to the membrane opposite the opening in the intermediate wall is adapted to be shifted between positions at which it is spaced from the opening and also disposed within the opening. In this manner, pressure applied to the membrane causes the closure finger to enter the opening and permits a measured quantity of the dentifrice to be taken off from the lower compartment. This pressure applying means includes a lever pivoted to the bottom of the apparatus casing below the dispenser. Tube take-off means conveniently directs the dentifrice from the lower compartment into the apparatus liquid containing reservoir. Biasing means serves to return the membrane to a position at which the finger is extended away from the opening. In addition, air venting means are provided to permit air to enter the container to replace the dentifrice removed therefrom.

29 Claims, 12 Drawing Figures

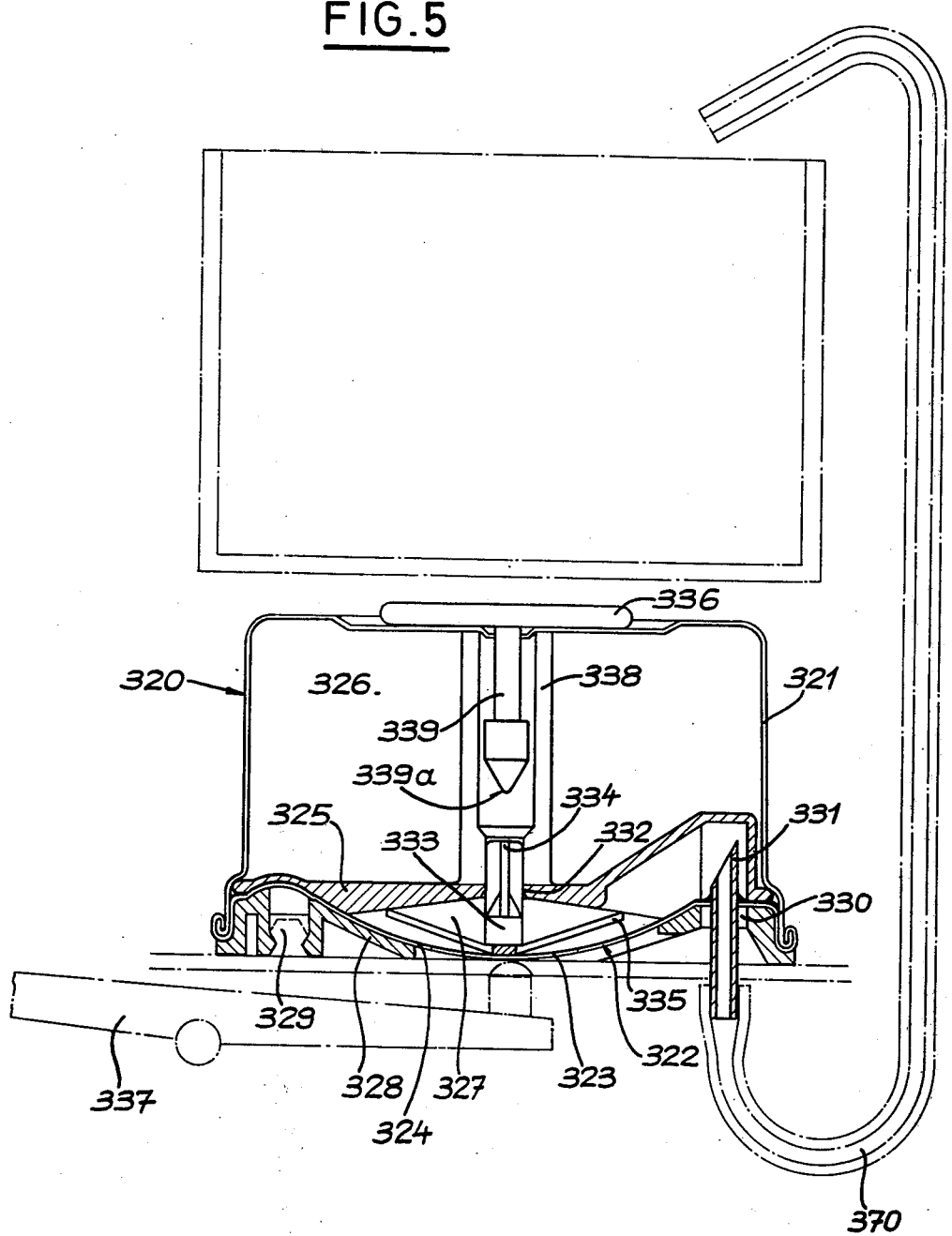

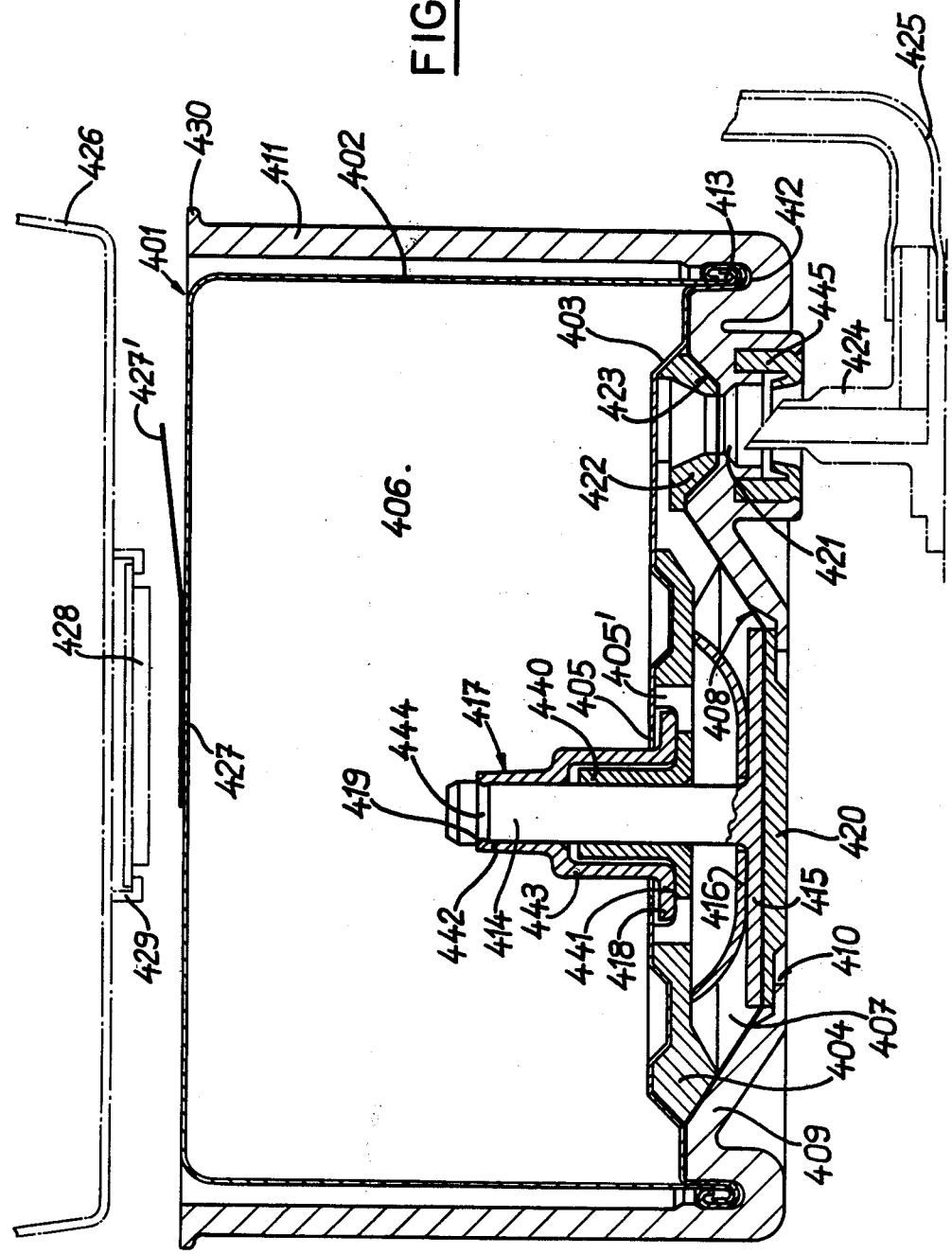

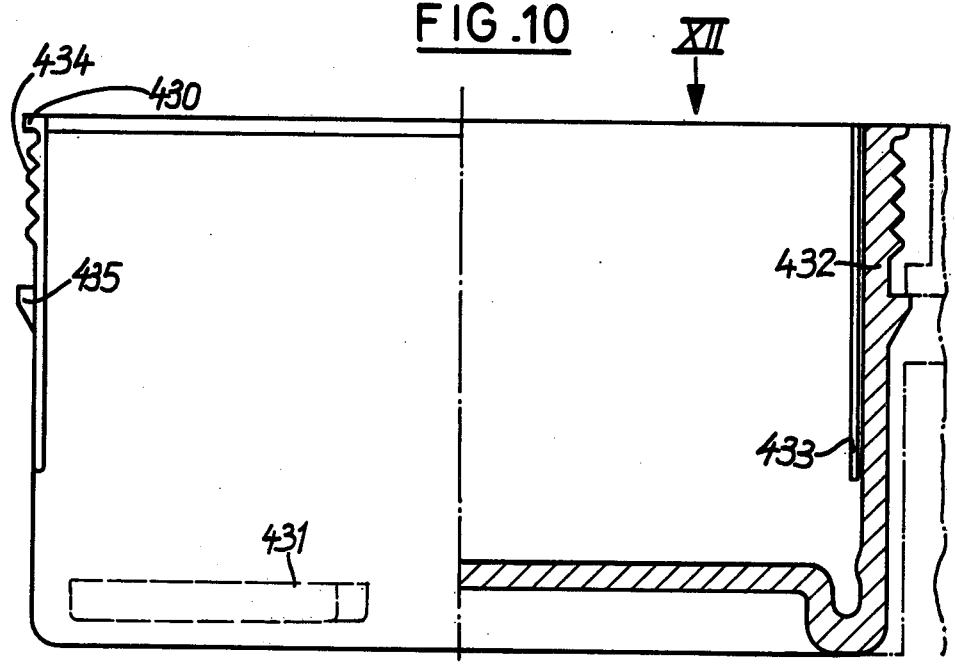
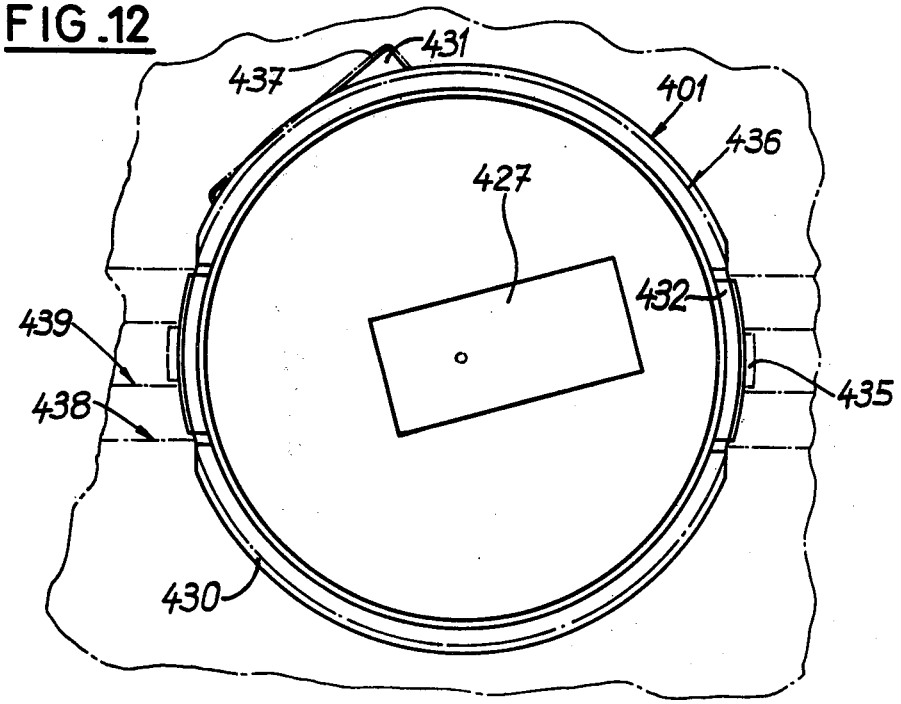

LIQUID TREATMENT APPARATUS FOR BODY CARE

REFERENCE TO RELATED APPLICATION

This application is a continuation-in-part of application Ser. No. 704,330 filed July 12, 1976 and now U.S. Pat. No. 4,078,558.

BACKGROUND OF THE INVENTION

There are commercially available liquid treatment apparatus for body care, and particularly for buccodental hygiene. Such apparatus generally includes a casing enclosing a hydraulic pump connected by a flexible tubing to a handpiece having a spray head, and a reservoir removably fitted on the casing for supplying liquid to the pump. This type of apparatus providing a pulsed jet of liquid is efficient both for cleaning the teeth and flushing out particles stuck between the teeth as well as for massaging the gums and stimulating blood circulation therein. In some "combined" apparatus, the spray nozzle can be replaced by a toothbrush which is oscillated by a hydraulic motor housed in the handpiece. In both of these types of devices, the reservoir is removably connected to the pump inlet by a suitable valve to supply water to the pump independently of the water supply. In certain types of apparatus the reservoir is formed by a removable cover which is reversible to receive the water and to connect with the pump to provide the water supply. Other alternative forms include a reservoir with a gripping handle and a pivoted lid with the reservoir resting on a lateral projection on the casing and being of shape and dimensions to complete the geometrical configuration of the casing. The content of such a reservoir may be from ½ liter to 1 liter of water, which is sufficient for the buccal treatment in question, and makes handling easy, even for children.

It has also been proposed to use dentifrice for prophylactic purposes and prevention of dental plaque this becoming ever increasingly necessary in view of the fact that 98% of the population suffers from dental decay and more than 90% of persons in the over 40 age group suffer from peridontal disease despite all of the dental hygiene measures taken to date.

Long research and practical experience have shown that chlorhexidine solutions are the most efficient products for this purpose. Tests have shown that concentrations slightly less than 0.2% of chlorhexidine gluconate can substantially delay the formation of dental plaques, and in particular a concentration of 0.025 to 0.5% is sufficient to obtain an excellent hygiene. The distribution of chlorhexidine to the different parts of the teeth and the consequent prevention of the formation of dental plaque may also be improved by use of an oral irrigation device. Further, it has been observed that the coloring effect which may occur because of the presence of chlorhexidine is considerably reduced if large volumes of low-concentration liquid are also used. Tests have shown that 700 ml of 0.1% chlorhexidine solution does not produce any more coloration than a neutral liquid whereas 20 ml of 0.2% solution produces an apparent coloration.

To achieve perfect mouth hygiene it would thus be possible to use the two aforesaid means, in turn, i.e., on the one hand, cleaning the teeth and massaging the gums by an apparatus of the described type, and on the other hand rinsing with a dentifrice solution. However, to achieve such complete hygiene would require several time consuming operations. People, usually in a hurry, in general sacrifice relatively little time for body care and in particular buccal hygiene, to the detriment of their health and prophylaxis. In fact, experience has demonstrated that it is unrealistic to expect people to regularly carry out such successive operations.

SUMMARY OF THE INVENTION

With the above background in mind, it is among the primary objectives of the present invention to provide as a totally new concept apparatus of the type described that is capable of efficient buccodental treatment and prophylaxis without increasing the time of treatment while simplifying overall treatment. To this end, an apparatus of the aforementioned type is characterized in that it incorporates means for receiving a dispenser of a hygienic, cosmetic or therapeutic product, in particular a dentifrice solution, for addition to the liquid in the reservoir. In a preferred embodiment these incorporated means for placing the dispenser comprise a housing situated below the reservoir, and the apparatus has means for connecting the outlet of the dispenser to the interior of the reservoir and means for actuating said dispenser.

Furthermore with the apparatus of this invention it is proposed to provide a dispenser for an additive which is particularly suited to combatting dental plaque, but which is in the form of a viscous sticky liquid that tends to clog up the dispenser when in general use.

In order to avoid this problem the dispenser according to the invention comprises a container closed at the bottom by a flexible membrane and with an intermediate wall located above said membrane defining upper and lower compartments in the container, said intermediate wall having an opening therein to provide communication between the two compartments, means for removing the product contained within the lower compartment, a closure finger attached to the inside surface of said flexible membrane at a point opposite the opening so that pressure exerted on the membrane causes the closure finger to enter said opening and permits a measured quantity of product to be taken off from the lower compartment, said means for actuating said dispenser comprising a lever pivoted to the bottom of the casing below the dispenser.

BRIEF DESCRIPTION OF THE DRAWINGS

With the above objectives among others in mind, reference is had to the attached drawings in which:

FIG. 5 shows another embodiment of the dispenser installed in the apparatus in the ready position;

FIG. 9 is a sectional view of another embodiment of the dispenser not in use, with the lower part of the reservoir shown in dot-dash lines, which is intended to be mounted on the latter and the outlet means connected to the apparatus;

FIG. 10 is a view in elevation and half section of the casing of the dispenser with the wall of the cavity of the apparatus in which the dispenser is intended to be mounted, shown in dot-dash lines;

FIG. 12 is a view in the direction of arrow XII of FIG. 2 with the cavity of the apparatus in which the dispenser is intended to be mounted shown in dot-dash lines.

DETAILED DESCRIPTION OF THE EMBODIMENT

The embodiments shown in FIGS. 1 to 4 allow for the use of a dispenser which is particularly suited to dispensing viscous or sticky liquid like chlorhexidine, which has properties particularly suited to combatting dental plaque.

Figure 1:
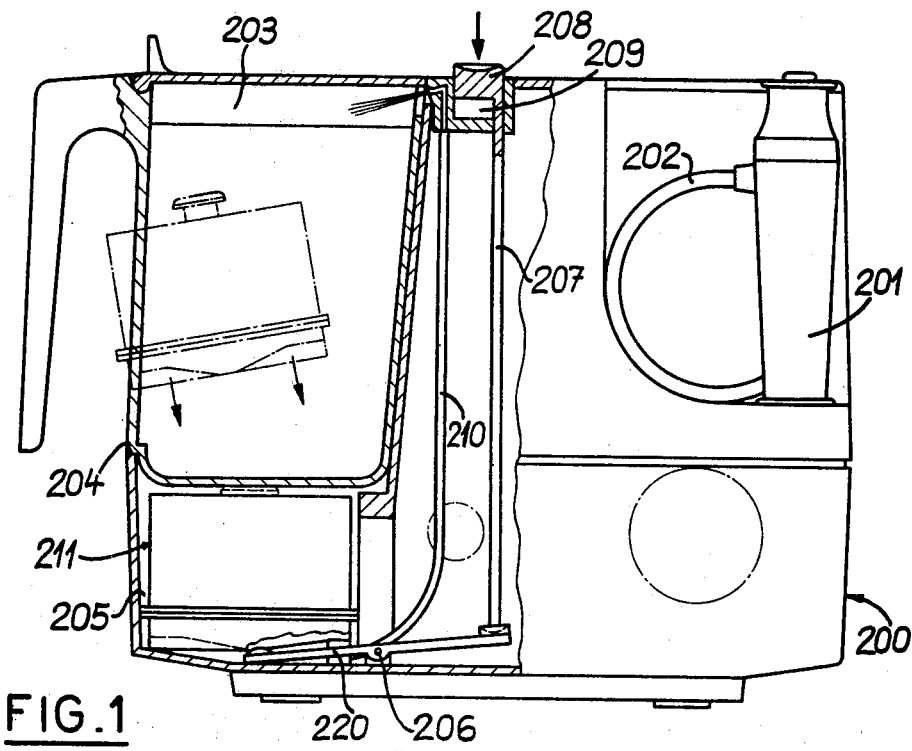
FIG. 1 is a front view of an embodiment of the invention including a schematic partial cross-section through the reservoir, the dispenser and the means for actuating the dispenser, the dispenser for use with this apparatus being shown in chain-dotted outline.
Figure 2:
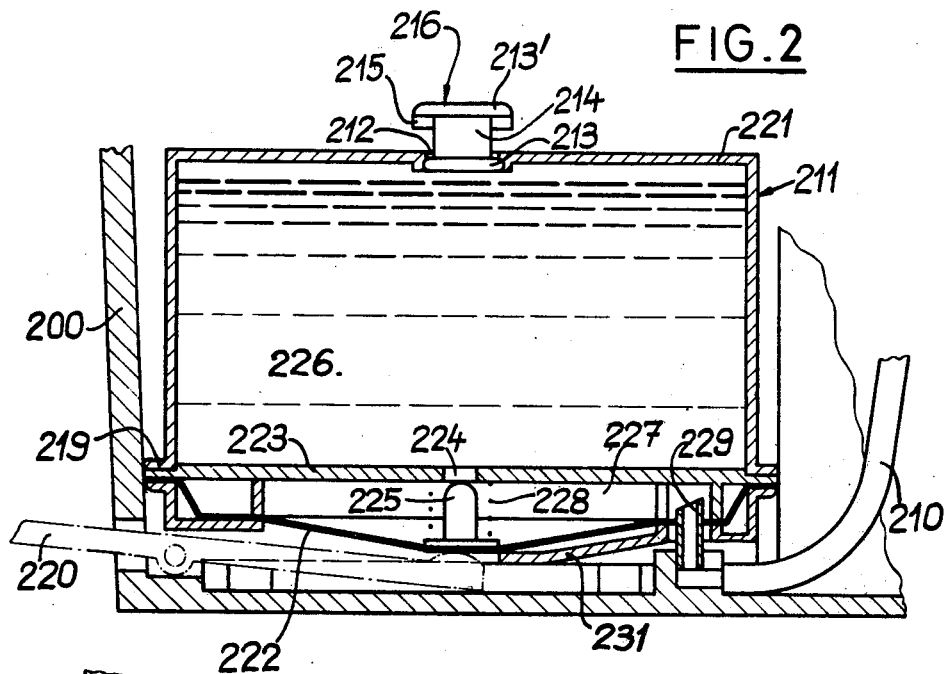
FIG. 2 is a side view, in cross-section, showing the dispenser in its rest position, and showing one form of the dispenser actuating means as seen from the side opposite that seen in FIG. 1.
Figure 3:
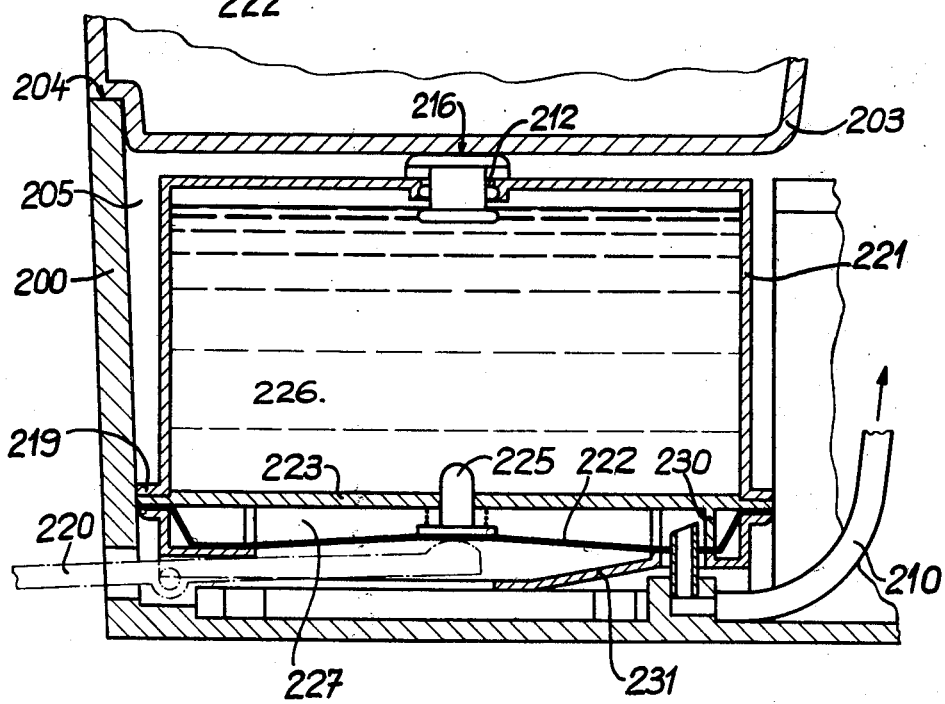
FIG. 3 is the same view as FIG. 2, but showing the dispenser mounted in the apparatus and in its operated position.

The apparatus of FIGS. 1 to 3 comprises a casing 200 in which is mounted a hydraulic pump with its electric motor, a handpiece 201 connected by flexible tubing 202 to the hydraulic pump, and a reservoir 203 supported on a laterally projecting portion 204 of the casing. Within this laterally projecting portion 204 is a housing 205 for a dispenser 211. The dispenser 211 is shown twice, the representation of it in chain-dotted outline showing how it is fitted in position when the reservoir 203 has been removed, as will be explained below.

At the bottom of the casing 200 is a lever 220 which pivots about an axis 206, one end being located at the bottom of the housing 205, beneath the dispenser 211, while the other end is coupled by a push-rod 207 to a push-button 208 located in a housing 209 in the top of the casing. The outlet orifice of the dispenser 211 is connected by a tube 210 to an outlet passage formed in the side wall of the housing 209 and directed into the reservoir 203.

The dispenser consists of a container 221 made from a rigid or semi-rigid material, such as a plastics material, closed at the bottom by a flexible membrane 222. Above the membrane 222 is a rigid intermediate wall 223 which divides the container 221 into an upper compartment 226 and a lower compartment 227. Opposite a hole 224 in the intermediate wall 223, the membrane 222 carries a closure finger 225; with the membrane 222 in its rest position, as shown in FIG. 2, the finger 225 is clear of the hole 224, so that communication between the upper and lower compartments 226 and 227 of the container 221 is unimpaired. When the membrane 222 is urged towards the intermediate wall 223, as shown in FIG. 3, the finger 225 closes off the hole 224, shutting off communication between the upper chamber 226 of the container 221 and the lower chamber 227 defined by the intermediate wall 223 and the membrane 222. The closure finger 225 is fitted with a return spring 228 which returns it to the rest position, clear of the hole 224, when the pressure on the membrane 222 is released. Means are provided for taking off the contents of compartment 227, consisting of a hollow needle 229 fixed to the bottom of the casing 200, with a bevelled tip which pierces the membrane 222 to create a seal around the needle and without detaching any small pieces of membrane which might block the liquid circuit; the other end of the needle is connected to the tube 210, along which the liquid passes towards its delivery point. The needle 229 pierces the membrane 222 at a point which is surrounded by a hollow, cylindrical boss 230 on the lower face of the intermediate wall 223 and open on one side. A rigid outer wall 231 is also provided, to protect the membrane 222, and has an opening through which the end of the lever 220 passes.

The top wall of the container 221 is provided with means for admitting air as the level of liquid in the container drops. These means comprise an opening 212 in the top wall of the container, closed by a closure element 216 which extends above said wall and can be moved towards the inside of the container in order to admit air thereto. The closure element 216 consists of two circular plates 213 and 213' joined by a central stem 214, the upper plate 213' having a diameter greater than that of the opening 212, and its lower face having radial ribs 215 thereon; the lower plate 213 is designed to close the opening 212 when the closure element then cutting off communication between the inside of the container and the atmosphere. When the device is operated, the closure element is pressed towards the inside of the container and the lower plate 13 ceases to close off the opening 212, so that air can freely enter between the ribs 215.

A peripheral flange 219 on the container 221 locates it within its housing 205.

The dimensions of the housing 205 for the dispenser 211 are such that the closure element 216 is opened as soon as the reservoir 203 is placed on the casing 200 of the apparatus, ready for use. The element 216 may be closed manually or by conventional return means.

When the apparatus is used, the dispenser 211 is placed in its housing 205 and the reservoir 203, filled with water, is placed on the laterally projecting portion 204 of the casing, pressing down the closure element 216, towards the inside of the upper compartment 226 of the dispenser 211 to admit air thereto. By pressing the push-button 208, as shown by the arrow in FIG. 1, the end of the lever 220 underneath the dispenser is raised. Pressure is therefore exerted on the flexible membrane 222, which rises to move the closure finger 225 to a position in which it closes off the opening 224 providing communication between the compartments 226 and 227 of the dispenser; the pressure exerted on the membrane 222 drives the product from the compartment 227, and through the needle 229, tubing 210 and outlet passage into the reservoir 203.

When the pressure on the push-button 208 is relaxed, the return spring 228 returns the lever to its rest position, as shown in FIG. 1. By way of modification, and in order to facilitate the return of the lever to its rest position, the push-button may be provided with a return spring located in the housing 209, beneath the button, for example, or beneath the lever 220.

Other means of operating the dispenser may be provided, for example, as shown in FIGS. 2 and 3, a lever passing out of the casing through an opening and which could be operated directly, without the intermediary of a push-button.

Figure 4:
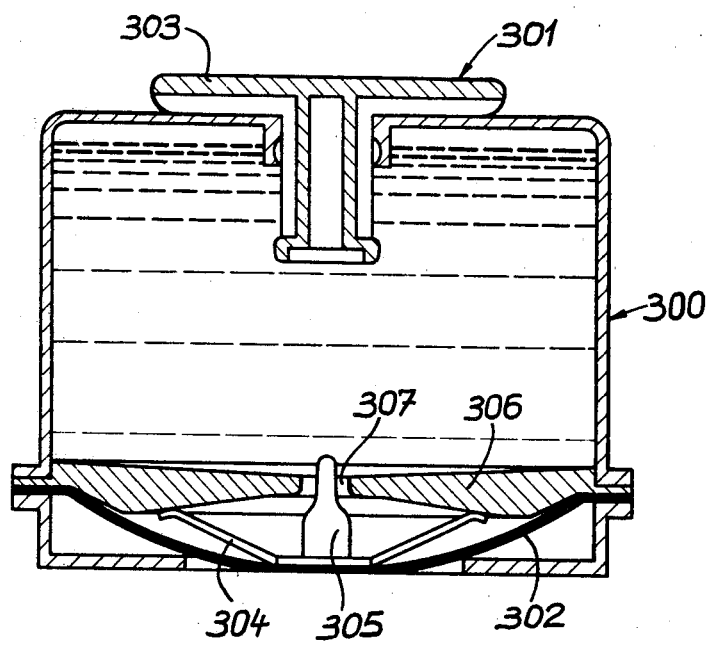
FIG. 4 is a view in cross-section of another embodiment of the dispenser, the means for removing the product therefrom not being shown.

Other modifications may also be made without department from the scope of the invention. For example, as shown in FIG. 4, the dispenser 300 could be provided with a closure element 301 designed to provide an adequate seating for the container to be placed thereon. To this end, the closure element 301 is relatively tall, as compared with the dispenser, and has a very wide top portion 303 on which the container can easily be stood; the stem of the closure element is longer than in the first embodiment.

Another modification, also shown in FIG. 4 is to use a ring washer 304 as the return spring for returning the membrane 302 to its rest position, the washer 304 bearing on the membrane 302 and on the intermediate wall 306.

Also, the closure finger 305 may have a tip with a diameter smaller than that of the opening in the intermediate wall 306, and be so arranged that in the rest position the tip passes with clearance through the hole 307 to allow the product to pass freely therethrough, the lower portion forming the closure finger proper, which closes off the hole.

Figure 6:
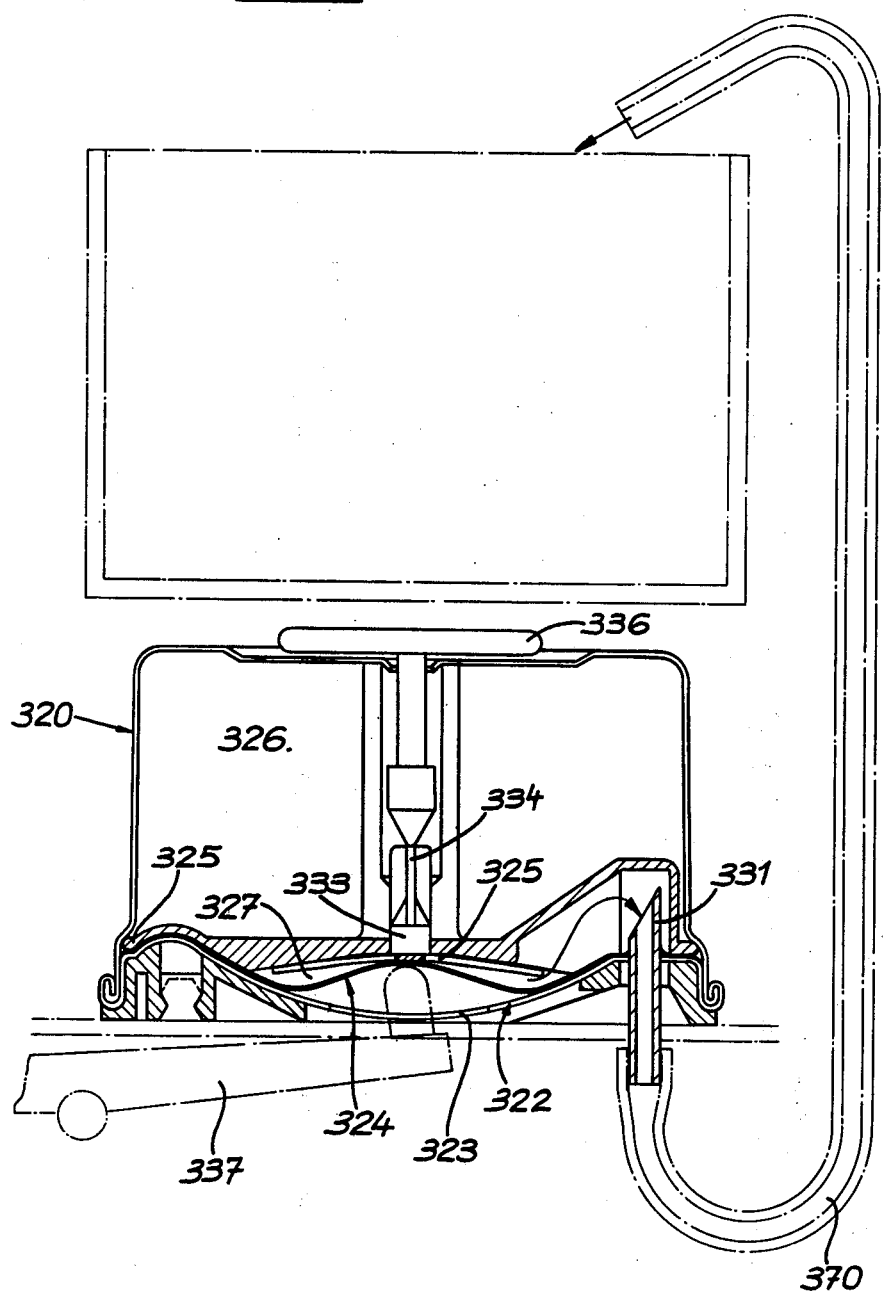
FIG. 6 represents the same view as FIG. 5, but with the dispenser in the operated position.

Referring to FIGS. 5 and 6, the dispenser 320 consists of a container 321 made of a rigid material such as sheet metal or aluminium, with a crimped bottom 322 in the center of which is an opening 323. A flexible membrane, made, for example, of aluminium foil covered on both sides with a plastics material, such as polypropylene, for example, has its edge gripped between the bottom 322 and the wall of the container 321. As in the preceding embodiments, a rigid intermediate wall 325 divides the container 321 into an upper compartment 326 and a lower compartment 327. A rigid plastics protective cover 328 is fitted over the bottom 322, and also has a central opening. The protective bottom cover 328 forms part of the container, and comprises means for fixing the container into the apparatus.

For example, the container may be designed to press fit onto a projection in the bottom of the apparatus, the rigid protective cover 328 being formed with corresponding recesses designed to retain the projection.

The protective cover 328 is also formed with an opening 330 through which passes the neddle 331 for removing the product from the dispenser when the latter is in position ready for use.

The upper and lower compartments 326 and 327 communicate with one another via an opening 332 in the intermediate wall. Attached to the inside of the flexible membrane 324 at a point opposite the opening 332 is a closure member 333 with an extension 335 which has a cruciform cross-section. Resilient tongues 335 attached to the bottom of the closure member 333 return the membrane to its rest position, replacing the return springs used in preceding embodiments.

The top of the dispenser is hermetically sealed when the dispenser is supplied, as is the point at which the needle 331 enters. When the dispenser has been fitted into the apparatus and the needle 331 has pierced the membrane 324 to enable the product in the dispenser to be removed, it is necessary to provide some means for admitting air to the inside of the dispenser. For this purpose a separate bung 336 is provided, and has a stem 339 with a tip 339a designed to pierce the top of the container 321. Once an opening has been made in this way, the bung 336 is left in position, closing off this opening to prevent evaporation of the product.

To admit air into the upper compartment 326 when a metered dose of the product is removed by means of the lever 337 as in the preceding embodiments, the design of the closure extension 334 and the stem 339 of the bung 336 is such that, when the bung 336 is pressed home in the opening 332, the raising of the extension 334 causes the bung 336 to be raised a few millimeters.

In a preferred embodiment of the invention, the intermediate wall 325 is provided with a central tube 338 which has longitudinal slots for guiding the pointed stem of the bung 336 as it is pushed in to pierce the top of the container 321, and for increasing the rigidity of the container as a whole.

Figure 7:
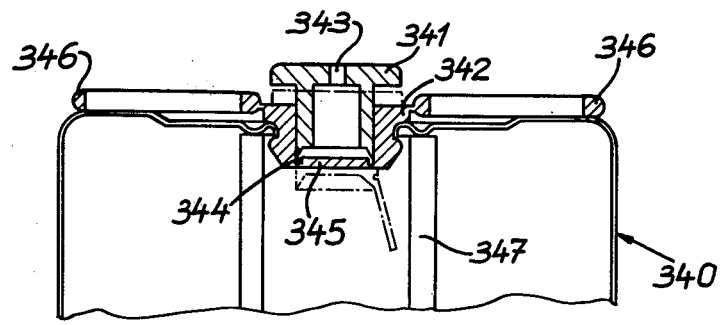
FIG. 7 is a partial view in cross-section of another embodiment of the upper part of the dispenser, the closure element being shown in chain-dotted outline in the operated position.

The dispenser 340 shown in FIG. 7 has an upper bung 341 which has an interference fit in a ring 342 attached to the top of the container. The bung and the ring are preferably of a plastics material. The bung 341 is hollow and closed at the top except for a small hole 343 for admitting air from the outside. The rim 344 at the bottom of the bung 341 has a sharp edge. When the container is supplied, the bung is in a raised position and the membrane 345 formed integrally with the ring 342 intact, so that the container is hermetically sealed. Once the dispenser has been fitted to the apparatus and is to be used, the container is opened by pressing in the bung 341, the sharp edge of the rim at the bottom of the bung cutting through the membrane 345 as shown in dotted outline, to allow air to enter the container. In a preferred embodiment of the invention the membrane is not cut through right around its perimiter in order to prevent it falling into the container. This can be achieved by making the membrane extra thick at one point, for example, or by providing an interruption in the sharp edge on the bung.

Another variation shown on this embodiment is the provision of two rings 346 at diametrically opposite points on the ring 342 and integral with it. These provide something to grip when an exhausted dispenser is to be removed from the apparatus.

The bottom of the container (not shown) is identical to that of the preceding embodiment, except that the slotted tube 347 is of larger diameter, to suit the diameter of the opening in the top of the container.

Figure 8:
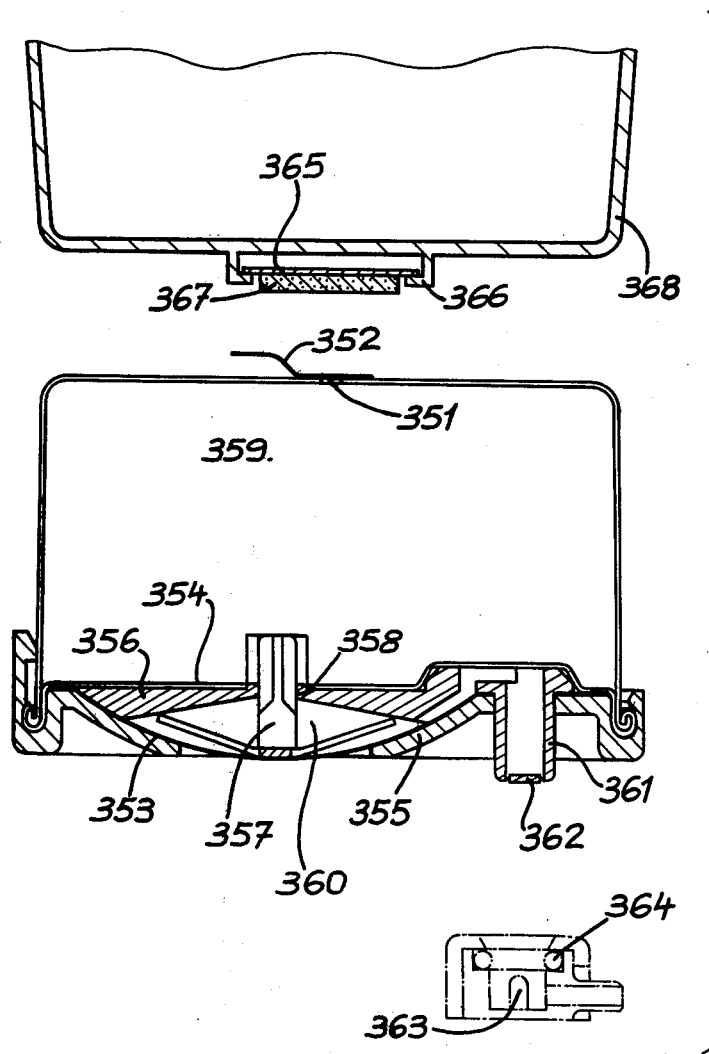
FIG. 8 shows another embodiment of the dispenser and the lower part of the reservoir, the product take-off means attached to the apparatus being shown in chain-dotted outline.

In the embodiment shown in FIG. 8, the container is of sheet metal and has a small hole 351 in the top, this being closed until the dispenser 350 is ready for use by a tear-off strip 352.

In this embodiment, the flexible membrane 353 is outside the metal bottom 354, and is merely sandwiched between the intermediate wall 356 and the plastics protective cover 355. This arrangement has advantages when it comes to manufacturing the dispenser and deep drawing the membrane, eliminating the risk of tearing the membrane as it is formed and fixed in place.

As in the preceding examples, the protective bottom cover 355 has a central opening through which passes the end of the lever (not shown). A closure member 357 is located so as to close off the opening 358 providing communication between the upper compartment 359 and the lower compartment 360.

FIG. 8 also shows another embodiment of the means for removing the product from the lower compartment 360. These include a tube 361 permanently attached to the protective bottom cover 355. When the dispenser is new and unused, the end of the tube 361 is closed by a thin membrane 362 which is pierced by a projecting portion 363 of the casing of the apparatus as the dispenser is fitted into the apparatus, an O-ring 364 providing a seal. With this arrangement the product take-off means take up less room.

With the two preceding embodiments, when the apparatus is not in use the holes 343 and 351 can remain open if they are small enough, i.e. about 1 mm in diameter, and if the product in the dispenser is not too volatile. With larger holes and more volatile products, the holes must be stopped up when the apparatus is not in use. For this purpose, a small metal plate 365 is held removably in grooves 366 formed in the bottom of the reservoir 368, with vertical of clearance. A small piece 367 of plastics foam is attached to the plate 365. Thus, when the reservoir is placed on top of the dispenser, the weight of the plate 365 presses the foam 367 into contact with the top of the dispenser and closes off the hole in it. The hole 351 is therefore closed off as soon as the reservoir is placed on the dispenser, even if the reservoir is not very accurately positioned on the dispenser. Air is admitted into the container each time the reservoir is raised from the apparatus to be filled with water.

The volume of the lower compartment of the dispenser is such that sufficient product is dispensed each time the membrane is actuated, taking account of the fact that some of the product remains in the tube 370 (FIG. 5).

Furthermore, when the lever is released the closure member does not immediately open up the hole providing communication between the two compartments of the dispenser, so that some of the liquid left in the take-off tube is sucked back as the membrane returns to its rest position. The volume of this tube must therefore be sufficient to prevent air bubbles being drawn into the lower compartment during this period.

The embodiment according to FIGS. 9 to 12 is characterized by the fact that a valve is provided, mounted by friction around the closure finger, this valve being entrained by the finger in both directions and its movement being limited by two fixed stops, an upper stop such that when it is pressed against the latter, said opening between the two compartments is closed and when it is moved away from the latter, said opening is clear and a lower stop which limits the travel of the valve on the finger.

Thus, as soon as the closure finger begins to move towards its inoperative position entraining the valve as it travels, the latter immediately clears the opening between the two compartments. This arrangement thus guarantees instantaneous filling of the lower compartment from the upper compartment when the membrane returns to its inoperative position and prevents the occurrence of suction of the column of liquid and possibly air which is located in the outlet pipe connected to the outlet orifice.

The dispenser 401 is composed of a cylindrical box 402 of rigid material, for example aluminium, provided with a metal base 403 which is clipped on, which rests on an intermediate wall 404 of plastics material. The metal base 403 is provided with a circular opening 405 whereas the intermediate wall 404 is provided with four equidistant openings 405' (FIG. 11), these openings 405 and 405' connecting the upper compartment 406 of the dispenser defined by the inside of the box 402 and a lower compartment 407 defined by the intermediate wall 404 and a flexible membrane 408 outside the box 402. The flexible membrane 408, constituted for example by a sheet of aluminium having a thickness of 12μ covered on one side by a layer of polyamide having a thickness of 15μ and on the other side by a layer of polyethylene having a thickness of 80μ is retained at its periphery by being gripped between the metal base 403 and a plastics base 409 for protecting the dispenser, provided with an opening 410. Mounted to move vertically in this opening 410 is a pusher-disc 420 by means of which it is possible to press on the membrane 408. The protective base 409 is connected to a cylindrical wall 411 which surrounds the box 402 and extends over the same height as the latter. An inner peripheral groove 412 is provided between the protective base 409 and the cylindrical wall 411, in which groove the rib 413 for clipping the base of the box 402 is force-fitted.

A closure finger 414 of plastics material (FIG. 9) connected to a washer 415 at its lower part is fixed on the inner side of the membrane 408 opposite the openings 405, 405' for connecting the upper and lower compartments 406, 407 respectively.

Figure 11:
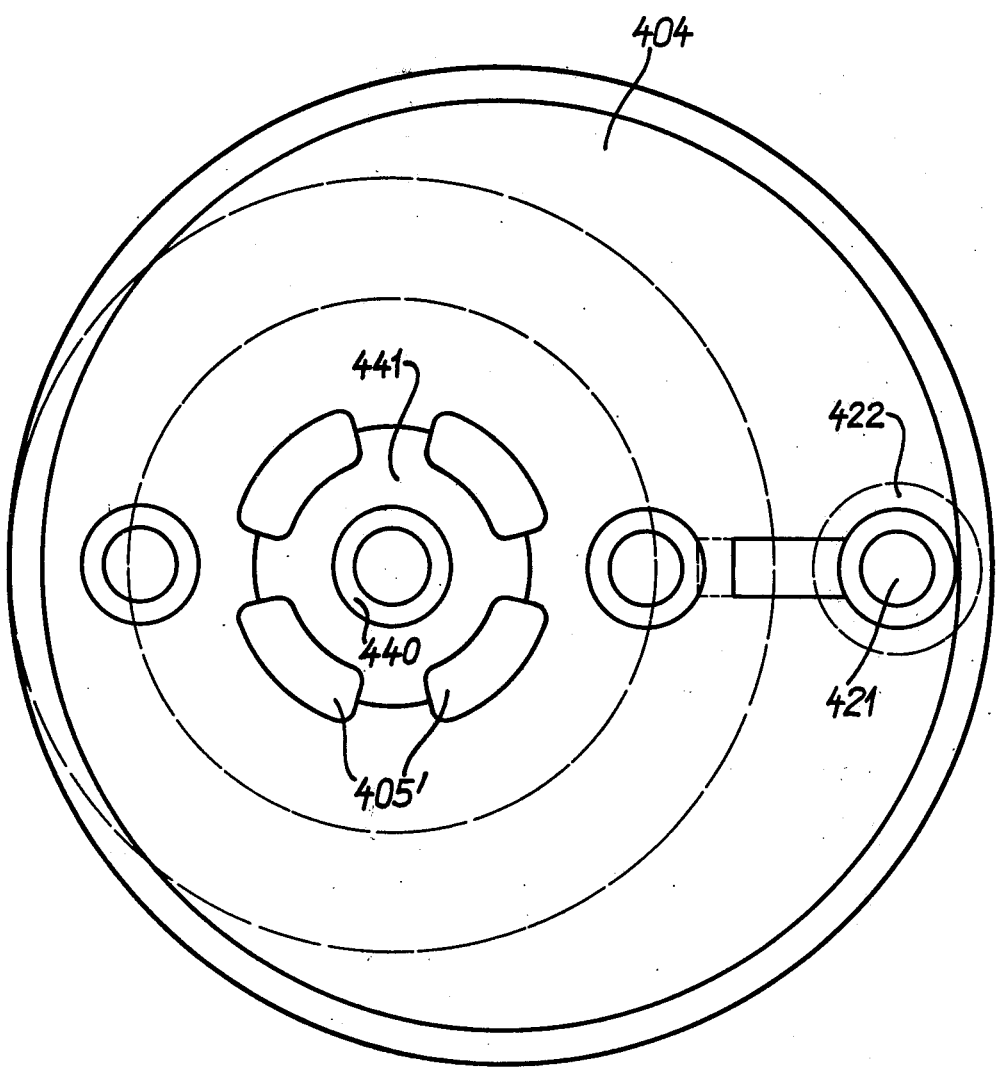
FIG. 11 is a plan view of the separating wall between the two compartments.

A plate-spring 416 comprising a hole is mounted on the finger 414 against the washer 415 in order that its two ends bent towards the inside of the compartment 407 press against the lower side of the intermediate wall 404. As a variation, this return spring could be constituted by resilient tongues cut in the washer and raised in the direction of the finger. As it moves, the closure finger 414 is guided by a hollow cylindrical boss 440 formed in one piece with the intermediate wall 404, said wall also being provided around this guide boss 440 with a cylindrical recess 441. As shown in FIG. 11, the connecting openings 405' are formed a straddle the recessed part 441 of the intermediate wall 404 and the solid part.

The length of the closure finger 414 is such that it passes through the opening 405 whatever the position of the flexible membrane 408. The diameter of this finger 414 is less than that of the opening 405 and a sliding valve 417 is mounted on the latter by friction in order to be entrained by the latter in both directions at the time of movement of the flexible membrane 408.

The valve 417 is formed by a tube 442 which fits on the finger 414 and by a circular head 418 whose diameter is greater than the diameter of the opening 405 in the metal base 403, but slightly less than the diameter of the recess 441 in the intermediate wall 404 so that the openings 405' in said wall 404 are always left clear. A small radial rib 419 is provided at the end of the tube 442 of the valve and engages in a resilient manner in a corresponding groove 444 formed at the end of the finger 414. An enlarged 443 surrounding the guide boss 440 of the finger 414 is provided between the tube 442 and the head 418. The travel of the valve 417 is very slight, of the order of 1 mm and its movement is limited by two stops, an upper stop constituted by the metal base 403 itself and a lower stop constituted by the central part of the intermediate wall 404.

The operation of the device is as follows: starting from the inoperative position shown in FIG. 9, if pressure is exerted on the pusher-disc 420 for ejecting a measured quantity of product, the membrane 408 deforms, thus reducing the volume of the lower compartment 407 and simultaneously, the finger 414 is moved upwards and as it travels entrains the valve 417 by virtue of the co-operation of the rib 419 and the groove 444. Whereas the valve 417 has completed its short travel, i.e. when its head 418 abuts against the metal base 403 and closes off the opening 405 between the lower and upper compartments 407 and 406 respectively, the closure finger 414 continues its upwards travel sliding in the valve, the radial rib 419 of the valve thus being disengaged from the groove 444, under the thrust, owing to the elasticity of the valve which is preferably made of plastics material. Owing to the fact that the passage 405 between the two compartments 406,407 is closed, the result of the compression of the lower compartment is to eject a measured quantity of product through the orifice 421 and an outlet pipe 425, as will be described hereafter.

When the pressure exerted on the pusher-disc 420 is released, the reserve movements take place, namely under the effect of the spring 416, the finger 414 drops, immediately entraining the valve 417 in its travel, by virtue of the frictional force which exists between the two parts, until the head 418 of the valve 417 bears against the base of the recess 441 of the wall 404. The finger 414 thus continues to drop still under the action of the spring 416 until it resumes its inoperative position in which the rib 419 once more engages in the groove 444. Owing to the fact that the head 418 of the valve 417 instantaneously clears the opening 405 for connection between the two compartments at the time of the return movement of the finger 414, the passage of the product between the two compartments is thus immediate, which prevents any suction of the column of liquid or possibly of air located in the outlet pipe 425.

Furthermore, the engagement by means of the rib 419 and groove 444 between the valve 417 and the finger 414 increases the frictional force between these two members in their inoperative position and prevents the valve head 418 from being stuck against the base of the recess 441 when the device is used, in particular when it is first used. Naturally, in order that the device operates, it is necessary that the return force of the spring 416 is greater than the frictional force between the finger 414 and the valve 417.

The dispenser which has just been described is intended to be placed in an apparatus for oral hygiene provided, for example as shown in FIG. 1, with a lever which raises the flexible membrane 408 for the ejection of a measured quantity of product. In view of the fact that the major central part of the membrane 408 is clamped between the pusher-disc 420 and the washer 415 integral with the closure finger 414, the latter prevents partial deformation of this membrane 408 under the action of the lever and an ejection of an incomplete measured quantity of product. The pusher-disc 420 presses against a large part of this membrane and, in the inoperative position, is retained by its stepped edge on the periphery of the opening 410 in the protective wall 409.

As shown in FIG. 9, the orifices 405 and 410 are off-centre with respect to the axis of the dispenser in order to leave a free space for the outlet orifice 421 which, when the device has not yet been used, is closed by the flexible membrane 408 which is compressed in the region of this orifice 421 between a boss 422 formed on the lower surface of the intermediate wall 404 which fits in a housing of complementary shape 423 provided on the upper surface of the protective wall 409. When the dispenser is put in position in the apparatus, the part of the membrane 408 closing off the orifice 421 is torn by a hollow needle 424 fixed to the apparatus and connected to an outlet pipe 425 connecting the outlet orifice 421 to the inside of a container 426 intended to receive the product, a sleeve-shaped gasket 445 ensuring the seal between the outlet orifice 421 and the hollow needle 424 which it surrounds.

Provided on the upper part of the box 402 is a small opening 427 for the passage of air, which is closed by a small tongue 427' which can be torn off when the device has not yet been used.

As described in relation with the embodiment shown in FIG. 8, the bottom of the reservoir 426 intended to rest on the box 402 is provided with a small cushion of foam 428 stuck to a metal plate and able to be moved by gravity in the grooves 429 formed on the bottom of the reservoir in order to closs off the opening 427 in order to prevent evaporation of the product.

The dispenser 401 is also provided with means enabling it to be positioned exactly in the apparatus for oral hygiene with which it is used. FIGS. 9 and 10 show that the upper end of the cylindrical wall 411 surrounding the box 402 is provided with a flange 430 projecting outwards and which serves for positioning the dispenser 401 axially in the appropriate cavity of the apparatus.

Furthermore, an asymmetrical projection 431 (FIG. 10) formed on the outer side of the cylindrical wall 411 makes it possible to position the dispenser 401 in an angular manner in the apparatus in order to guarantee perfect alignment of the outlet orifice 421 and the outlet means of the apparatus.

Furthermore, the cylindrical wall 411 is provided with two diametrically opposed resilient tongues 432 defined by longitudinal cut-outs 433 in the wall 411. The upper end of these tongues 432 is provided on its outer side with horizontal ridges 434 enabling the user to grip the dispenser 401 between two fingers. Furthermore, a locking projection 435 intended to be fitted in appropriate openings in the apparatus is also provided below the ridges 434.

The apparatus for oral hygiene intended to receive the dispenser (FIG. 19) is thus provided with a cavity 436 of appropriate dimensions and such that the dispenser fits inside, the wall of this cavity comprising an asymmetrical groove 437 intended to receive the asymmetrical projection 431 and diametrically opposed recesses 438 corresponding to the location of the resilient tongues 432 and facilitating the passage of the user's fingers for removing or positioning the dispenser.

Openings 439 are provided below these recesses for receiving the projections 435 of the tongues 432, said projections being able to be introduced into these openings by virtue of the elasticity of the tongues which may be deformed radially inwards, the return of the tongues to the inoperative position once the dispenser has been put in position ensures locking of the dispenser in the cavity owing to the projections 435 which abut against the upper wall of the openings 439.

The useful volume of the dispenser is approximately 80 to 90 $cm^3$ and the metered quantity of product ejected by one action on the pusher-disc 420 is approximately 0.5 $cm^3$, which allows the dispenser to be used approximately 200 times.

The apparatus has been described in relation to use for buccodental hygiene, but it is clear that similar apparatus, possibly merely with appropriate modifications in the spray head, may be used for the treatment of other parts of the body, for example, the nose, ears or for local massages. In this case, the product in the dispenser for addition to the liquid in the reservoir could, as before, be a hydgienic product, or alternatively be a therapeutic or cosmetic product.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

What is claimed is:

1. Apparatus for personal hygiene, in particular for oral hygiene comprising:
a casing, a reservoir fitted on the casing for containing a liquid supply, a dispenser of an additive for addition to the liquid in the reservoir, the casing including means for receiving the dispenser, the receiving means comprises a housing situated below the reservoir, means for connecting the outlet of the dispenser to the interior of the reservoir, and means for activating said dispenser.

2. Apparatus in accordance with claim 1, wherein the casing encloses a hydraulic pump connected by a flexible tubing to a handpiece, the reservoir being removably fitted on the casing fur supplying liquid to the pump, and the additive being a hygienic, cosmetic or therapeutic product.

3. Apparatus in accordance with claim 1, wherein the dispenser is removable and replaceable.

4. Apparatus in accordance with claim 1, wherein said dispenser comprises a container closed at the bottom by a flexible membrane and with an intermediate wall located above said membrane defining upper and lower compartments in the container, said intermediate wall having an opening therein to provide communication between the two compartments, means for removing the product contained within the lower compartment, a closure finger attached to the inside surface of said flexible membrane at a point opposite the opening so that pressure exerted on the membrane causes the closure finger to enter said opening and permits a measured quantity of product to be taken off from the lower compartment, said means for actuating said dispenser comprising a lever pivoted to the bottom of the casing below the dispenser.

5. Apparatus in accordance with claim 4, wherein said lever is coupled by a push-rod to a push-button which is located in a housing on the upper surface of the casing, and wherein means are provided for returning the push-button to its rest position.

6. Apparatus in accordance with claim 4, wherein said closure finger has a tip with reduced cross-section passing through said opening in the intermediate wall.

7. Apparatus in accordance with claim 4, wherein means are provided for returning the membrane to its rest position.

8. Apparatus in accordance with claim 7, wherein said return means consist of a spring washer fitted between said flexible membrane and the intermediate wall.

9. Apparatus in accordance with claim 1, wherein the means connecting the outlet of the dispenser to the inside of the reservoir comprise a tube connected to a passage in the casing with its outlet directed towards the reservoir.

10. Apparatus in accordance with claim 9, wherein said means for removal of the product contained in the dispenser comprise a hollow needle connected to said tube and fixed to the bottom of the casing, its length being such that it pierces said membrane, when the dispenser is in position, at a point which is surrounded by an open, hollow boss on the lower surface of the intermediate wall.

11. Apparatus in accordance with claim 4, wherein the dispenser has in its upper wall an opening which is normally closed by a closure element which extends above said upper wall and can be moved towards the inside of the container to admit air thereto as the level of the product therein drops, and in that the dimensions of said housing are such that when the reservoir is placed on the apparatus, ready for use, it bears on said closure element and presses it down towards the inside of the container to admit air to said container.

12. A dispenser for use as part of an apparatus for personal hygiene which includes a reservoir for containing liquid, the dispenser being adapted to retain a dentifrice therein and to dispense the dentifrice therefrom upon demand, and comprising means on the dispenser for cooperating with complementary means on the apparatus to position the dispenser with respect to the apparatus so that dentifrice can be dispensed from the dispenser into the liquid in the reservoir of the apparatus, the dispenser comprising a container closed at the bottom by a flexible membrane and with an intermediate wall located above said membrane defining upper and lower compartments in the container, said intermediate wall having an opening therein to provide communication between the two compartments, means for removing the product contained within the lower compartment, a closure finger attached to the inside surface of said flexible membrane at a point opposite the opening so that pressure exerted on the membrane causes the closure finger to enter said opening and permits a measured quantity of product to be taken off from the lower compartment, said means for actuating said dispenser comprising a lever pivoted to the bottom of the casing below the dispenser.

13. A dispenser in accordance with claim 12, wherein it is hermetically sealed until required for use and comprises means for making a hole in its top for admitting air when it is to be used.

14. A dispenser in accordance with claim 13, wherein said hole is formed in the dispenser during manufacture and is sealed until the dispenser is required for use by means of a tear-off strip welded to the dispenser.

15. A dispenser in accordance with claim 13, wherein the dispenser is manufactured with a hole in its top closed by a ring and a membrane, a hollow closure member being located in the ring and having a sharp lower edge so that on pressing in the closure member the sharp edge cuts through the membrane, an air inlet hole being provided in the closure member.

16. A dispenser in accordance with claim 13, wherein said hole is closed by the reservoir when the latter is in position in the apparatus and open when the reservoir is removed, the bottom of the reservoir preferably having a pad of foam mounted on a metal plate retained with sufficient clearance in grooves on the bottom of the reservoir to be movable up and down therein.

17. A dispenser in accordance with claim 12, wherein the opening in the dispenser is made by means of a separate closure member having a tip for piercing, the closure member remaining in position in the dispenser once the opening is formed and being lifted in the axial direction by an extension of the closure finger when the latter enters the opening providing communication between the upper compartment and lower compartment, in order to admit air to said upper compartment.

18. A dispenser in accordance with claim 12, wherein the lower compartment and the product removing means are connected together by means of a tube attached to the bottom of the dispenser and opening into said lower compartment, the tube being closed until the dispenser is required by use by a membrane which is pierced by a projection in the casing when the dispenser is fitted into the casing.

19. A dispenser in accordance with claim 12, wherein the flexible membrane consists of an aluminum foil covered on each side with a plastics material.

20. A dispenser in accordance with claim 12, wherein the upper portion of the dispenser is provided with two pull-rings, preferably of a plastics material, for gripping the dispenser when it is empty and is to be removed from the apparatus.

21. A dispenser in accordance with claim 12, wherein a valve is provided, mounted by friction about the closure finger, this valve being entrained by the finger in both directions and its movement being limited by two fixed stops, an upper stop such that when it is pressed against the latter, said opening for connection between the two compartments is closed and that when it is moved away, said opening is clear and a lower stop which limits the travel of the valve on the finger.

22. A dispenser in accordance with claim 21, wherein the valve comprises a tubular part which fits on the finger and a head whose diameter is greater than said opening for connecting the two compartments and which moves between said lower and upper stops.

23. A dispenser in accordance with claim 22, wherein the intermediate wall is provided with a hollow cylindrical boss serving to guide the finger and surrounded by a cylindrical recess the base of which constitutes said lower stop for the valve, openings passing through said wall being provided astraddle the wall of the cylindrical recess and its base.

24. A dispenser in accordance with claim 23, wherein the closure finger is connected at its lower end to a washer and that a plate-spring is mounted on said finger against said washer such that its free ends bear against said intermediate wall in order to serve as a spring for returning the membrane to its inoperative position.

25. A dispenser in accordance with claim 24, wherein a protective base is provided below the membrane, which base has an opening in which a pusher-disc able to move against the action of the spring is mounted and that the central part of said membrane is clamped between the lower side of the washer and the upper side of said pusher-disc.

26. A dispenser in accordance with claim 25, wherein the dispenser is cylindrical and that is is surrounded by a protective wall in one piece with the protective base, said wall being provided at its upper end with a flange directed outwards and in its lower region with an asymmetrical projection also projecting outwards and that two resilient tongues are cut in said wall, these two tongues being longitudinal, diametrically opposed and provided at the end of their outer side with a lateral projection and horizontal ridges.

27. A dispenser in accordance with claim 24, wherein the closure finger is provided at its upper end with an annular groove, engaging resiliently in which is a radial rib formed inside the end of the tubular part of the valve in order to increase the frictional force between the finger and the valve in their inoperative positions.

28. A dispenser in accordance with claim 21, wherein when the dispenser has not yet been used, said outlet orifice is closed off by said flexible membrane which is compressed at this point between a boss formed on the lower surface of the intermediate wall which fits in a housing of complementary shape provided on the upper surface of the protective wall.

29. Apparatus in accordance wih claim 1, comprising a dispenser in accordance with claim 26 and a cylindrical recess whose diameter corresponds to the outer diameter of the wall for protecting the dispenser such that the flange of the dispenser rests on the periphery of this recess, the wall of the cylindrical recess being provided with an asymmetrical longitudinal groove for the passage of the asymmetrical projection of the dispenser and two diametrically opposed openings intended to receive the projections of the tongues, these two openings being surmounted by a recess to facilitate gripping of the dispenser by means of the two tongues which may be deformed radially in width.

* * * * *